US011723556B1

(12) United States Patent
Hamilton

(10) Patent No.: US 11,723,556 B1
(45) Date of Patent: Aug. 15, 2023

(54) INSTRUCTIONAL TECHNOLOGIES FOR POSITIONING A LOWER LIMB DURING MUSCULAR ACTIVITY AND DETECTING AND TRACKING PERFORMANCE OF A MUSCULAR ACTIVITY

(71) Applicant: University of Houston System, Houston, TX (US)

(72) Inventor: Marc T. Hamilton, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 17/878,036

(22) Filed: Jul. 31, 2022

Related U.S. Application Data

(60) Provisional application No. 63/391,197, filed on Jul. 21, 2022.

(51) Int. Cl.
*A61B 5/11* (2006.01)
*A61B 5/00* (2006.01)

(52) U.S. Cl.
CPC .......... *A61B 5/1107* (2013.01); *A61B 5/1121* (2013.01); *A61B 5/6829* (2013.01); *A61B 5/742* (2013.01)

(58) Field of Classification Search
None
See application file for complete search history.

(56) References Cited

U.S. PATENT DOCUMENTS

| | | |
|---|---|---|
| 4,573,678 A | 3/1986 | Lamb et al. |
| 4,807,874 A | 2/1989 | Little |
| 4,967,736 A | 11/1990 | Spitzer |

(Continued)

FOREIGN PATENT DOCUMENTS

| | | | |
|---|---|---|---|
| EP | 2239540 A1 | 10/2010 | |
| WO | WO-2019175899 A1 * | 9/2019 | ........... A61B 5/0002 |

OTHER PUBLICATIONS

Bojsen-Møller, Jens, et al. "Differential displacement of the human soleus and medial gastrocnemius aponeuroses during isometric plantar flexor contractions in vivo." Journal of applied physiology 97.5 (2004): 1908-1914. (Year: 2004).*

(Continued)

*Primary Examiner* — Benjamin S Melhus
(74) *Attorney, Agent, or Firm* — Shackelford, Bowen, McKinley & Norton, LLP

(57) ABSTRACT

A soleus contraction measurement system includes a sensor configured to measure rotational movement when positioned on a user's foot with an X-axis oriented laterally across the user's foot, a Y-axis oriented parallel to the user's foot, a Z-axis orthogonal to the X-axis and the Y-axis, and a positive X-axis rotational movement corresponding to an increasing ankle angle, and a memory storing computer-executable instructions for controlling a processor to: measure an X-axis rotational movement, identify a positive X-axis rotational movement as a plantarflexion and a negative X-axis rotational movement as an ankle dorsiflexion, deem the plantarflexion a performed soleus contraction when the plantarflexion is immediately followed by the ankle dorsiflexion for two consecutive cycles of plantarflexion and ankle dorsiflexion, and cause performance information regarding the performed soleus contractions to be communicated.

5 Claims, 9 Drawing Sheets

(56) References Cited

U.S. PATENT DOCUMENTS

| | | | |
|---|---|---|---|
| 5,203,321 | A | 4/1993 | Donovan et al. |
| 5,284,465 | A | 2/1994 | Homan, Jr. |
| 5,558,606 | A | 9/1996 | Poncini et al. |
| 6,569,213 | B1 | 5/2003 | Busch |
| 7,403,144 | B1 | 7/2008 | Cruz-Albrecht et al. |
| 7,857,733 | B2 | 12/2010 | Tsakiris |
| 8,280,679 | B2 | 10/2012 | Maxwell et al. |
| 8,460,163 | B2 | 6/2013 | Gibbons |
| 8,827,843 | B2 | 9/2014 | Priester et al. |
| 10,406,395 | B2 | 9/2019 | Haas |
| 10,434,357 | B2 | 10/2019 | McCarthy |
| 10,589,141 | B2 | 3/2020 | Shimizu et al. |
| 10,702,740 | B2 | 7/2020 | Tarkington et al. |
| 10,774,371 | B2 | 8/2020 | Mohrman et al. |
| 10,939,850 | B2 | 3/2021 | Roberts et al. |
| 11,207,559 | B2 | 12/2021 | Tarkington et al. |
| 11,259,707 | B2 | 3/2022 | Yuen et al. |
| 11,278,765 | B2 | 3/2022 | Mohrman et al. |
| 11,284,804 | B2 | 3/2022 | Ng et al. |
| 2010/0279835 | A1* | 11/2010 | Ozawa ............... A63B 21/068 482/148 |
| 2013/0303947 | A1* | 11/2013 | Gamet ................... A61B 5/11 600/595 |
| 2014/0039571 | A1* | 2/2014 | Wolpaw ............... A61B 5/742 607/45 |
| 2015/0100251 | A1* | 4/2015 | Solinsky ............. G01L 9/0073 702/33 |
| 2015/0265449 | A1* | 9/2015 | Togninalli ............. A61F 5/012 602/13 |
| 2016/0100801 | A1* | 4/2016 | Clark .................. A61B 5/7278 73/865.4 |
| 2016/0287937 | A1* | 10/2016 | Fitzgerald ............... A43B 3/34 |
| 2017/0100586 | A1* | 4/2017 | Akiba .................... A61B 5/224 |
| 2017/0312515 | A1* | 11/2017 | Ferree ............... A61N 1/36021 |
| 2019/0231223 | A1* | 8/2019 | Takagi ................. A61B 5/1116 |
| 2020/0008745 | A1* | 1/2020 | Burch, V ............... G16H 50/30 |
| 2020/0030604 | A1* | 1/2020 | Ferree ............... A61N 1/36021 |
| 2020/0093400 | A1* | 3/2020 | Hamner ............. A61N 1/0484 |
| 2020/0367823 | A1* | 11/2020 | Chahine ................ A41B 11/00 |
| 2020/0390389 | A1* | 12/2020 | Soe ....................... G16H 40/67 |
| 2021/0259579 | A1* | 8/2021 | Grant-Beuttler ..... A61B 5/1038 |
| 2022/0183588 | A1* | 6/2022 | Fukushi ............... A61B 5/6807 |
| 2022/0183592 | A1* | 6/2022 | Oliveira Santos ..... A61B 5/684 |
| 2022/0338759 | A1* | 10/2022 | Vidal ................... A61B 5/7242 |
| 2022/0409097 | A1* | 12/2022 | Gaskell ............... A61B 5/1122 |

OTHER PUBLICATIONS

Lauber B, Lichtwark GA, Cresswell AG. Reciprocal activation of gastrocnemius and soleus motor units is associated with fascicle length change during knee flexion. Physiol Rep. Jun. 11, 2014;2(6):e12044. doi: 10.14814/phy2.12044. PMID: 24920126; PMCID: PMC4208651. (Year: 2014).*

Takahashi KZ, Gross MT, van Werkhoven H, Piazza SJ, Sawicki GS. Adding Stiffness to the Foot Modulates Soleus Force-Velocity Behaviour during Human Walking. Sci Rep. Jul. 15, 2016;6:29870. doi: 10.1038/srep29870. PMID: 27417976; PMCID: PMC4945910. (Year: 2016).*

Johnson, L.; Validity and Reliability of Smartphone Magnetometer-based Goniometer Evaluation of Shoulder Abduction—A Pilot Study, http://www.elsevier.com/open-access/userlicense/1.0/, 2015, 22 pgs.

Halkar, M.; Inojosa, J. M.; Liedl, D.; Wysolinski, W.; Hougton, D. E.; Wennberg, P. W.; Lin, G.; Kane, G.; Fischer, K.; Rooke, T. W.; Sadiq, R.; Bonikowske, A.; McBane II, R. D.; Calf Muscle Pump Function as a Predictor of All-Caust Mortality. Vascular Medicine, 2020, vol. 25(6) 519-526.

Nilliamson, R; Andrews, B. J.; Detecting Absolute Human Knee Angle and Angular Velocity Using Accelerometers and Rate Gyroscopes. Medical & Biological Engineering & Computing 2011, vol. 39, 294-302.

Manivasagam, K.; Yang, L.; Evaluation of a New Simplified Inertial Sensor Method against Electrogoniometer for Measuring Wrist Motion in Occupational Studies. Sensors 2022, 22, 1690, 12pgs. https://doi.org/10.3390/s22041690.

Feldhege, F.; Mau-Moeller, A.; Lindner, T.; Hein, A.; Markschies, A.; Zettl, U. K.; Bader, R.; Accuracy of a Custom Physical Activity and Knee Angle Measurement Sensor System for Patients with Neuromuscular Disorders and Gait Abnormalities. Sensors 2015, 15,10734-10752, 19pgs. https://doi.org/10.3309/s150510734.

Engstrand, F.; Tesselaar, E.; Gestblom, R.; Farnebo, S.; Validation of a Smartphone Application and Wearable Sensor for Measurements of Wrist Motions. Journal of Hand Surgery (European Volume), 2021, vol. 46(10) 1057-1063.

Tongnetti, A.; Lorussi, F.; Carbonaro, N.; De Rossi, D.; Wearable Goniometer and Accelerometer Sensory Fusion for Knee Joint Angle Measurement in Daily Life. Sensors 2015, 15, 28435-28455; doi:10.3390/s151128435.

Ruiz-Olaya, A. F., Callejas-Cuervo, M., and Lara-Herrera, C. N., Wearable low-cost inertial sensor-based electrogoniometer for measuring joint range of motion. DYNA 84(201), pp. 180-185, 2017.

Rigoni, M.; Gill, S.; Babazadeh, S.; Elsewaisy, O.; Gillies, H.; Nguyen, N.; Pathirana, P. N.; Page, R.; Assessment of Shoulder Range of Motion Using a Wireless Inertial Motion Capture Device—A Validation Study. Sensors 2019, 19, 1781, 8pgs.

* cited by examiner

INSTRUCTIONAL TECHNOLOGIES FOR POSITIONING A LOWER LIMB DURING MUSCULAR ACTIVITY AND DETECTING AND TRACKING PERFORMANCE OF A MUSCULAR ACTIVITY

TECHNICAL FIELD

This disclosure relates in general to the field of tracking physical activities, and more particularly, but not by way of limitation, to instructing muscle activity and detecting, monitoring, and/or tracking soleus contractions.

BACKGROUND

This section provides background information to facilitate a better understanding of the various aspects of the disclosure. It should be understood that the statements in this section of this document are to be read in this light, and not as admissions of prior art.

Health and fitness is an increasing concern as the population becomes more sedentary. It has been recognized by the inventor that plantarflexion movements performed in a specific fashion has heretofore unrecognized health benefits. Teaching the proper form for these movements and implementing proper performance of these movements can be difficult without trained staff and specialized, expensive equipment. There is a need and desire for devices and systems that can identify when the particular movements are being performed and to serve as a monitor and activity tracker.

SUMMARY

An exemplary soleus contraction measurement system includes a sensor configured to measure rotational movement when positioned on a user's foot with an X-axis oriented laterally across the user's foot, a Y-axis oriented parallel to the user's foot, a Z-axis orthogonal to the X-axis and the Y-axis, and a positive X-axis rotational movement corresponding to an increasing ankle angle, and a memory storing computer-executable instructions for controlling a processor to: measure an X-axis rotational movement, identify a positive X-axis rotational movement as a plantarflexion and a negative X-axis rotational movement as an ankle dorsiflexion, deem the plantarflexion a performed soleus contraction when the plantarflexion is immediately followed by the ankle dorsiflexion for two consecutive cycles of plantarflexion and ankle dorsiflexion, and cause performance information regarding the performed soleus contractions to be communicated.

An exemplary contraction system includes a sensor configured to measure rotational movement when positioned on a user's foot with an X-axis oriented laterally across the user's foot, a Y-axis oriented parallel to the user's foot, a Z-axis orthogonal to the X-axis and the Y-axis, and a positive X-axis rotational movement corresponding to an increasing ankle angle, a memory storing computer-executable instructions for controlling a processor to: measure an X-axis rotational movement, identify a positive X-axis rotational movement as a plantarflexion and a negative X-axis rotational movement as an ankle dorsiflexion, deem the plantarflexion a performed soleus contraction when the plantarflexion is immediately followed by the ankle dorsiflexion, and cause performance information regarding the performed soleus contractions to be communicated; and a base having a bottom surface extending along a horizontal plane, a placement surface for locating the user's foot, and a communication device configured to communicate the performance information.

An exemplary method operable by a processor of a measurement unit for monitoring plantarflexions includes measuring, with a sensor located on a user's foot, rotational movement about an X-axis, where the X-axis extends laterally across the user's foot, a Y-axis extends parallel to the user's foot, a Z-axis extends orthogonal to the X-axis and the Y-axis, and a positive X-axis rotational movement corresponds to an increasing ankle angle; identifying a positive X-axis rotational movement as a plantarflexion and a negative X-axis rotational movement as an ankle dorsiflexion; deeming the plantarflexion a performed soleus contraction when the plantarflexion is immediately followed by the ankle dorsiflexion for two consecutive cycles of plantarflexion and ankle dorsiflexion; and causing performance information regarding the performed soleus contractions to be communicated.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion. As will be understood by those skilled in the art with the benefit of this disclosure, elements and arrangements of the various figures can be used together and in configurations not specifically illustrated without departing from the scope of this disclosure.

DETAILED DESCRIPTION

Figure 1:
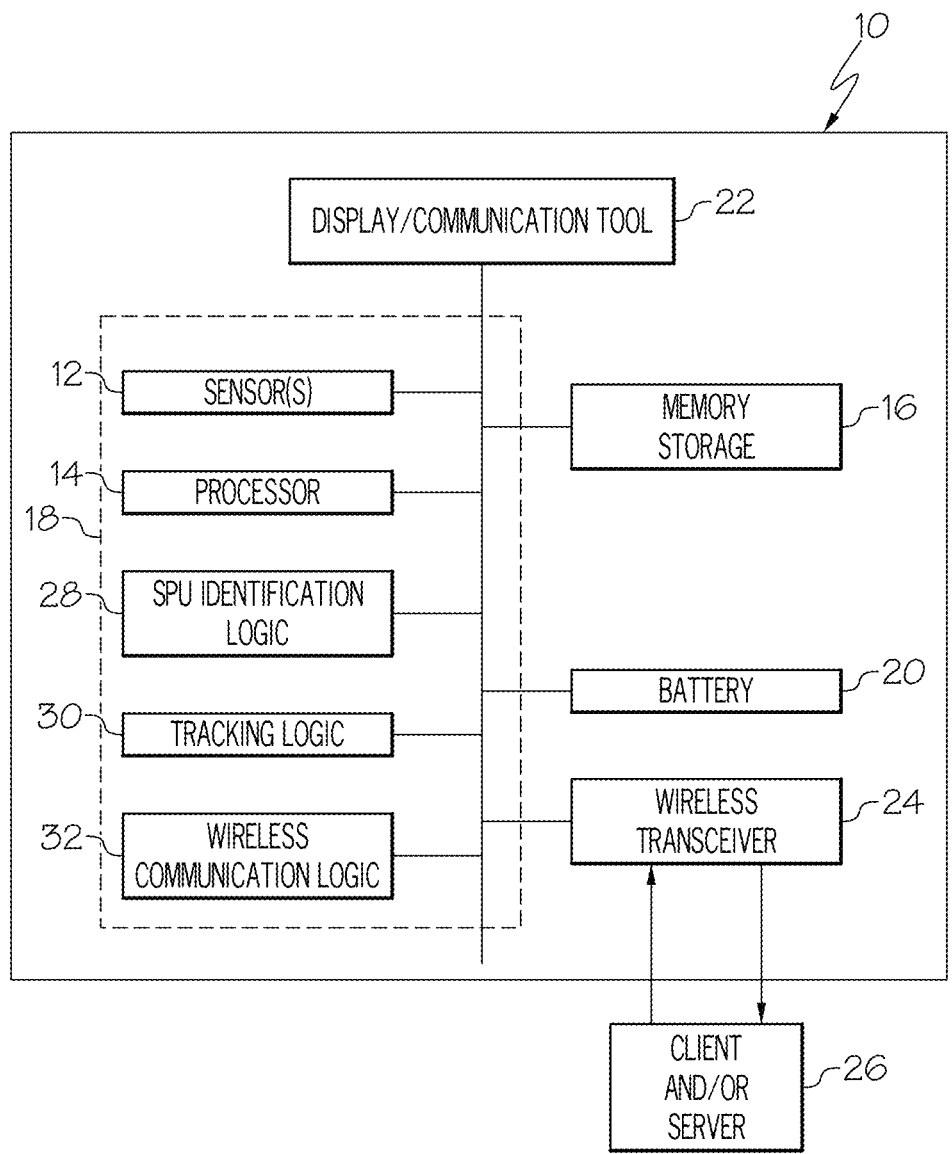
FIG. 1 illustrates an exemplary measurement and tracking system unit according to one or more aspects of the disclosure.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

The term "soleus push-up" (SPU) is used to denote a specific type of plantarflexion with a relatively high soleus electromyography (EMG) on-time (i.e., soleus activation) coinciding with upward angular motion of the ankle. Through unexpected experimental results, the inventor has developed novel methods of performing soleus contractions to achieve beneficial health effects. This method of soleus contraction and the resultant health effects have not heretofore been studied. In the studies and experiments the inventor used several types of expensive laboratory grade equipment not readily available for most clinicians, therapists, and laypersons. It is important to provide systems that are relatively inexpensive and easy to use, in order for the public to benefit widely from learning how to perform these novel soleus contractions. There are unique aspects of learning and tracking this small and low effort movement that utilize innovations disclosed herein.

These novel soleus contractions are a potent physiological method to enhance systemic lipid and glucose metabolism. Disclosed is a measurement unit with a wearable sensor, e.g., a gyroscope, that can be attached to the user's foot for quantitative monitoring of soleus contractions throughout the day in free-living conditions. The systems and methods can be used for instructing proper performance of soleus contractions and tracking these soleus contractions for the purpose of preventing and/or treating human metabolic and cardiovascular conditions responsive to soleus muscle contractions. The measurement unit can be used for identifying proper performance of a soleus contraction, for example to train a user in the proper position of the lower leg and foot and the proper movement, as well as tracking the performance of soleus contractions and distinguishing movements that qualify as the desired soleus contractions from other miscellaneous lower limb movements and vibrations including, without limitation, walking, tapping a foot, and riding in a vehicle. The measurement unit may distinguish between soleus contractions performed when standing and when sitting. Benefits of the soleus contractions are achieved in novel ways not associated with typical exercises. For example, effective soleus contractions can be achieved at lower rates (contractions/min) than at higher rates performed with the same range of motion (ROM). Additionally, effective soleus contractions are performed when seated and without adding resistance to the movement.

Prior to this disclosure, skilled practitioners did not have knowledge of these novel soleus contractions nor a reason to develop or construct soleus contraction measurement and monitoring systems and methods. This knowledge includes the ability to know what human movements to exclude from tracking. Plantarflexion is a general term of the process of ankle bending caused by contraction of the calf musculature. The inventor has identified that there are specific biomechanical parameters during one specific type of plantarflexion, that the inventor has developed, to isolate the soleus muscle from other muscles, which is remarkably superior in activating the soleus to a higher level than other types of plantarflexion such as walking. Surprisingly, it also provides an indefatigable method of sustaining human metabolism for prolonged periods when sitting comfortably. There are specific biomechanical parameters for how the soleus contractions can induce an intense metabolic stimulus during an SPU, unlike other types of plantarflexion that have previously been studied. Finally, there is knowledge regarding how to avoid misclassifying non-specific movement, e.g., car riding and walking, from the specific SPU movement and soleus contraction.

These soleus contractions can be performed when sitting. One reason there are physiological health gains by unique biochemical processes with this kind of treatment is because people can accomplish the SPU contractions frequently throughout the day. People sit on average ~10 hours/day, even more so in people at risk for chronic diseases impacted by muscular inactivity. The inventor has shown the real-world behavioral applicability and adaptive health benefits after one has been taught this behavior. A diverse group of adult participants voluntarily performed SPU contractions during normal daily sitting an average duration close to half of their total daily sitting time (5.3±0.4 hours/day, or ~35 hrs/week; N=32). That is remarkable compared to any other kind of physical activity. It is made possible by the ease of use, safety, and the fact the soleus muscle is indefatigable with this particular activity. The inventive systems and methods described herein will be essential for people to identify and track proper performance and the cumulative time proper soleus contractions are performed because people sit on average about 50-55 times per day and have little memory of each of those periods. The only way to make it feasible and accurate for people in the real world to track the quality of the SPU contractions and the magnitude of expected benefits is with the systems and methods disclosed herein.

Means to avoid errors in accurately capturing performed SPUs are disclosed based on problems and solutions identified by a large amount of empirical experimentation. One major source of error with activity trackers includes car riding, because it is a common behavior that involves sitting for long durations and car riding involves a high amount of vibration even on smooth roads. With only the use of accelerometers, which are more commonly used to track physical activity in general, it has been found that a high amount of error is introduced in discerning between SPU contractions and this non-specific vibration. A second problem solved was that with a gyroscope, the ROM overlaps between SPU contractions and car riding. This problem was solved by analysis of the duration and ROM of each singular movement to distinguish between non-specific movements and SPU contractions. Car driving causes many movements with a duration typically less than about 50 ms versus a duration greater than about 80 to 100 ms for the upstroke of even the high velocity SPU contractions.

The disclosed systems and methods can be used by clinicians to instruct patients how to perform SPU contractions, by non-experts to learn on their own how to perform proper SPU contractions, and to track daily SPU contractions. An advantage of using a gyroscope and possibly an accelerometer is that they are inexpensive and commonly available. Gyroscopes and accelerometers are mass produced and included with a magnetometer in what is known as an inertial measurement unit (IMU). For purposes herein, a measurement unit, or IMU, may include only a gyroscope or utilize only the gyroscope. Because an SPU contraction is a novel movement, no one previously has envisioned how a gyroscope can be used for the specific purpose of teaching and tracking this specific and unique type of soleus contraction. Typically, physical activity trackers use accelerometry and focus on measuring things like steps or total body acceleration. On the other end of the continuum, high end research grade equipment like electronic goniometers, electromyography, and indirect calorimetry are fragile and expensive. Devices described herein are more useful than that in a clinical setting and by the end users in the public. It is useful to teach the movement and to provide the user with immediate feedback, and daily summaries from an app on a phone or computer, for example of the position of the ankle and ROM of the ankle when sitting. One of the specific novel and practical aspects of the technologies is that instead of having to wear a pair of gyroscopes on two body parts to monitor the ROM of a joint, as is standard in biomechanics research, it is possible to only have to wear a single sensor, or sensor unit, to detect and measure SPU soleus contractions, if placed properly on the foot and using it as disclosed herein. Furthermore, by knowing the exact duration of each individual SPU movement and the velocity during a given ROM, e.g., 250 msec upstroke at a velocity of 180 deg/sec during a 45-degree ROM, the sensitivity and specificity can be high enough to discern the magnitude of intended benefits, while also avoiding artifact movements that take place during other human movements like walking, fidgeting, and car riding. This work involves distinguishing SPU soleus contractions from other types of movement, e.g., walking and car driving, in order to achieve a high level of specificity. Measurement units have sufficient sampling frequency and battery technology to be adapted for the novel purposes intended. If the measurement unit includes a magnetometer, the magnetometer may be turned off to save battery life. The software can, with the specific velocity of ankle movement, the duration, and/or ROM of each SPU movement, teach and track the SPU contractile activity.

In developing the SPU contraction, the inventor was originally thinking mostly about specific disease conditions closely related to muscular inactivity in the lower limb. For one, PAD (peripheral artery disease) is a vascular disease with a low rate of blood flowing through the arteries perfusing the legs. PAD can be painful and especially symptomatic in the calf musculature of the lower part of the legs, where the soleus is the predominant muscle. A second increasingly common, because of an aging and obese population, and often debilitating and painful condition like PAD is swelling in the lower legs and feet. Leg swelling/edema is a common disorder but difficult to treat. Neither PAD or edema are effectively treated with medications or surgeries as with other cardiovascular conditions. However, soleus muscle contractions are the most effective means to increase blood flow to the lower legs. Also, the soleus muscle pump is an effective mechanism to redistribute tissue fluid back to the heart and out of the limbs. Therefore, it is believed that the disclosed systems and method will be of great usefulness for these disorders. SPU contractions are the most comfortable and physiologically powerful type of soleus muscle contraction studied heretofore, and results show it can safely be taught and tracked quantitatively.

As described herein, the soleus muscle contractions have an especially important role in blood flow because the soleus has a phenotype different from other muscles such that it has the greatest capacity for flow of all muscles in the lower limb, and by being the most distal muscle away from the heart, it is the most important muscle for pumping on the veins to return fluid back to the heart and prevent leg/foot swelling in addition to vein disorders in the legs. The rate of blood flow in the leg is directly dependent on the metabolic rate of the soleus muscle. The rate of blood flow is elevated during walking, but there is now strong evidence that the increase in blood flow and muscle oxygen consumption is markedly greater during SPU contractions than when walking. In fact, it is calculated that the oxygen consumption by the SPU contractions is almost 10-fold greater in the recruited muscle mass than when walking. Secondly, because the SPU contractions do not induce fatigue, joint pain, and can be safely graded incrementally with the systems and methods disclosed herein, the SPU contractions will be an effective means for patients with PAD to titrate the stimulus of soleus metabolism to give an optimal magnitude of health benefit without the typical pain associated with walking. Finally, and related to this last point, the duration of SPU contractions is markedly greater than one is practically able to do with walking because most people sit 10 hours per day and SPU contractions can be done while sitting. Therefore, there is an abundant opportunity for patients to adhere to prescriptions for daily dosing of SPU contractions to improve their health.

The inventor's physiological and biochemical research has focused, in large part, on impaired glucose tolerance (IGT) and hyperinsulinemia in the postprandial period. IGT is the strongest metabolic risk factor for developing type 2 diabetes. IGT is often described as the most important clinical biochemical parameter determining health outcomes related to glucose disorders, Alzheimer's disease, some cancers, neuropathies, dyslipidemia, and cardiovascular conditions. It is also one of the most difficult risk factors to improve by medications or lifestyle approaches. However, the inventor has shown with SPU contractions there was on average about a 50 percent reduction in the postprandial glucose excursion in highly controlled laboratory studies. The research also demonstrated that the insulin concentration, which is not only involved in diabetes risk, but numerous other conditions including some cancers and cardiovascular health, was reduced at least as much as the glucose excursions. The research identified that the VLDL (very low-density lipoprotein) was markedly reduced in each individual tested within a single day (acute) of SPU contractions. VLDL has much implication not only for cardiovascular health, but also fat metabolism, liver health, and chronic inflammatory processes.

Notably, the research results describe a quantitative dose-response between the level of SPU contractions and the desired physiological response. Therefore, with the devices, systems, and methods described herein, people will be able to gauge their level of SPU contractions objectively in relation to potential health benefits. Important to this is the perception of effort expended during SPU contractions is not proportional to the dose of the SPU contractions, necessitating these technologies for quantifying the SPU contractions and thereby providing the user with feedback. Unlike most types of muscle contractions, e.g., weightlifting or bicycling, people were unable to accurately assess the relative effort of SPU contractions by the normal mind-muscle perceptions of effort. Normally the metabolic stress put on the muscle can be felt and people use this as a gauge for progressing in their exercise prescription. However, with SPUs, everyone finds it such a low effort behavior, that they are unsure of whether they are doing it correctly to bring about the large metabolic responses noted above and how to optimize the movement.

SPU contractions do not need external resistance, i.e., an unloading muscle contraction. This is only possible because of a specific biomechanical movement that can be taught and monitored with the technologies disclosed herein. This reduces fatigue, adds to safety, but does not reduce the metabolic cost of the activity. In a fatigue evaluation, the soleus activation, from electromyography (EMG), can be matched between SPU contractions and other types of plantarflexion such as standing heel lifts or sitting and doing plantarflexion against external resistance (a loaded muscle contraction). In each individual, there was a marked difference in the effort to do SPU contractions and the other types of plantarflexion commonly prescribed for exercise. When working at a soleus EMG (held steady at ~40% of EMG-max), standing heel lifts and seated loaded SPU contractions induced fatigue in these individuals within two minutes. The perceived effort increased gradually during the 120 second to the point of being unbearable to continue. In contrast, the SPU contractions were fatigue resistant such that the effort was perceived as very light. Even when doing the SPUs continuously immediately after the fatiguing types of plantarflexion, the SPU contractions were rated as a 1 on scale of 1-10, indicating low relative effort. Furthermore, over thirty individuals who were generally unfit and untrained were tested. With the specific instructions provided, the test subjects were able to comfortably sustain SPUs continuously for hours at a time without a sense of exertion or any adverse responses such as muscle cramps or joint pains. The activity is not stressful on the heart because the heartrate and blood pressure remain close to resting levels. This work was including subjects who often had a history of cardiovascular disease and therefore is a safe way to induce increases in muscular blood flow and cardiac stroke volume in the absence of a significant increase in blood pressure and heart rate that would be seen with traditional exercise. Important to all of this, the subjects would not have been able to learn the SPUs or maintain the SPU level without the feedback provided from knowledge of the range of motion and isolation of the soleus muscle contractions. On the contrary, when people were not provided with instructions for what a high-quality contraction is, people would often resort to a low-quality SPU that would not produce an adequate soleus EMG nor provide a superior increase in oxygen consumption, fat metabolism, and carbohydrate metabolism.

The SPU contractions produced unexpectedly marked improvements in key health related outcomes even in non-diseased healthy individuals. Because of this, widespread utilization of the devices, systems, and methods described herein is anticipated for people seeking better overall health. This includes a consistent doubling in whole-body fat metabolism throughout the entire day, a robust reduction in plasma VLDL-triglyceride acutely within a single day, and improved glucose tolerance and less hyperinsulinemia acutely within a single day. Proper performance of the soleus contractions as taught herein lead to health gains in otherwise normally healthy people. A study as identified how two months of performing SPU contractions voluntarily whenever the participants are sitting at work or at home led to reduced low grade systemic inflammation, improved biomarkers of liver metabolism, improved biomarkers of atherosclerotic cardiovascular disease, improved biomarkers related to disruptions caused by cellular iron metabolism, improved glucose regulation, reduced plasma insulin, and improved fat metabolism.

SPU contractions can be taught and monitored with the innovations described herein. This will provide a low-cost treatment to be used in multiple common debilitating medical applications, as well as for people concerned about improving their health to avoid disease.

FIG. 1 illustrates an exemplary soleus contraction measurement and monitoring unit, generally denoted with the numeral 10. The unit may include one or more separate components in operational communication with one another. Measurement unit 10 includes one or more sensors 12, a processor 14, a memory 16 storing computer-executable instructions 18 for controlling the processor, a battery 20, a communication device 22 (display and/or audible and/or tactile device), wireless transceiver 24, and a client and/or server 26. The instructions, or logic, 18 may include soleus push-up identification logic 28, tracking logic 30, and wireless communication logic 32.

Sensor 12 may consist only of a gyroscope. Sensor 12 can include a gyroscope and an accelerometer, which may be packaged together or configured for positioning in different locations from one another. Sensor 12 can be packaged as an inertial measurement unit (IMU) having a gyroscope, accelerometer, and a magnetometer. At least one sensor, for example the gyroscope is configured to be worn on a user's foot, for example on the top of the foot or the bottom of the foot.

Performance information regarding movements, in particular performance of particular soleus contractions, is communicated via communication device 22 to the user. The information may be communicated visually, audibly, and/or tactilely. Communication devices 22 may be located in different locations from the sensor, for example on a separate wearable device from the sensor, or on a smart phone, tablet, computer, and/or base station. In some embodiments, a base station includes a communication device 22 to communicate performance information. For example, the communication device 22 may include a visual display. In some examples, the base may include a tactile device that will communicate performance information via the user's foot, for example, that soleus contractions are being performed. An example of a tactile communication device includes a vibrating pad positioned at the user's forefoot on the base.

One or more of the components of measurement unit 10 can be located with and/or separate from the sensor that is positioned on the user's foot. For example, the processor, memory, and logic can be located remote from the sensor. For example, a measurement unit portion including for example the sensor, storage, and logic may be configured to be worn on a user's foot and be in communication, wirelessly or by wire, with a remote computing device and the internet. The remote computing device can support installation and execution of applications, such as activity tracking application that may be downloaded from a server. The remote device can be a smartphone, handheld computer, table computer, laptop computer, desktop computer, or other computing device interfacing with the wearable sensor.

Figure 2:
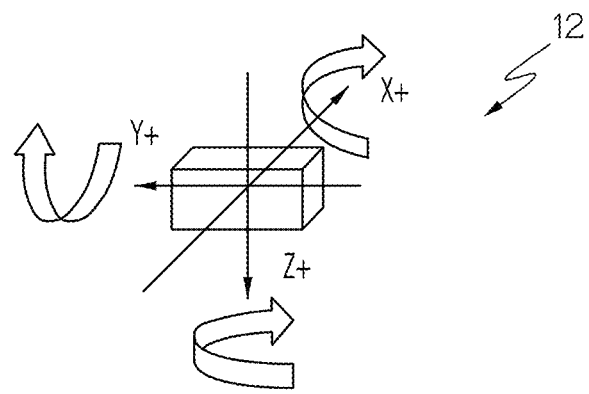
FIG. 2 illustrates a triaxial sensor and a three-axis frame of reference.

FIG. 2 illustrates an exemplary 3-axis inertial sensor 12, such as a gyroscope. In an exemplary embodiment, the monitoring unit includes a gyroscope to measure rotational movement. A triaxial gyroscope directly measures the angular velocity of rotation in 3 axes. From this, both the duration of each rotational movement and the range of motion (ROM) are determined with the measurement unit.

Figure 3:
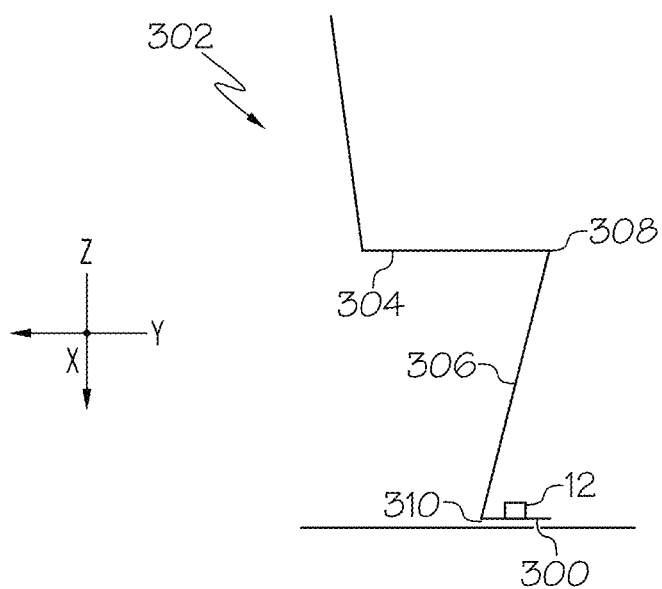
FIG. 3 schematically illustrates exemplary sensor locations on a user.

FIG. 3 schematically illustrates a user in an exemplary position for performing the subject soleus contractions and exemplary positions for sensors of a measurement unit. A triaxial sensor 12, in the form of a gyroscope, is worn on a foot 300 of a user 302 with the Y-axis aligned parallel to the foot from toe to heel, the X-axis extends laterally from side to side across the foot, and the Z-axis is parallel with gravity. FIG. 3 illustrates user 302 sitting with the thigh 304 generally parallel to the floor 315. When the X-axis is rotating, the back of the foot and leg 306 (shin) are rising. This action is thereby measuring ankle 310 extension, which is caused by the rotation of the ankle joint during the subject soleus contraction. Sensor 12 is positioned on the top or bottom of the foot, as opposed to the side of the foot, with the X-axis, as the primary axis of rotation, parallel to the floor and perpendicular to the sagittal plane or direction of gravity. When sensor 12 includes both a triaxial gyroscope and triaxial accelerometer, such as in a common inertial measurement unit, the position of sensor 12 can be calibrated knowing the orientation with the gravitational field from the triaxial accelerometer output. The sensor may be arranged so that X-axis rotational movements in a first direction, for example positive measurement outputs, correspond to an increasing ankle angle 316 (plantarflexions) and the X-axis rotational movements in a second direction, for example negative measurement outputs, correspond to a decreasing ankle angle (dorsiflexion).

Figure 4C:
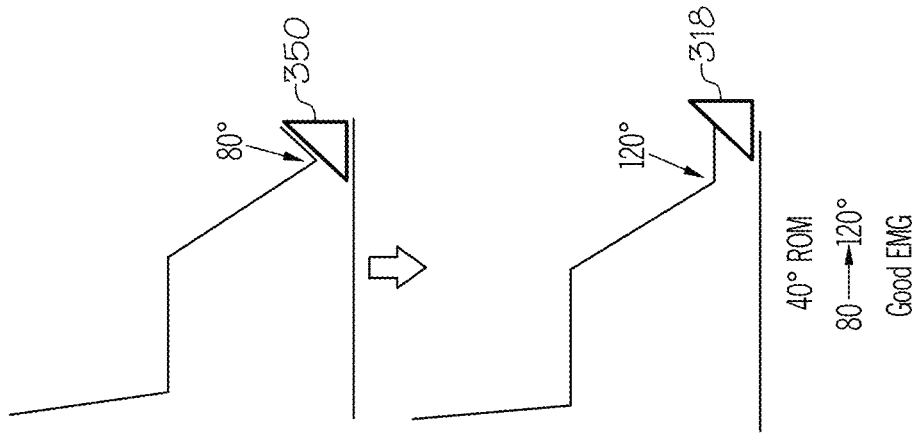
FIG. 4C schematically illustrates performance of an exemplary soleus contraction with the user's foot on a base station from a starting ankle angle to an ending ankle angle with a "good" soleus electromyography signal.
Figure 4B:
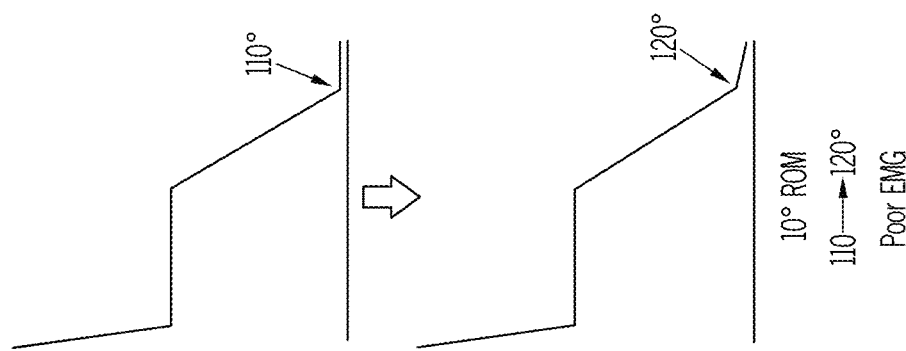
FIG. 4B schematically illustrates performance of an exemplary soleus contraction from a starting ankle angle to an ending ankle angle with a "poor" soleus electromyography signal.
Figure 4A:
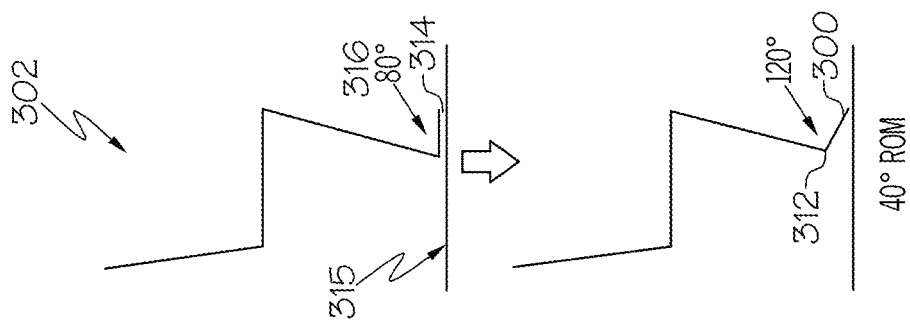
FIG. 4A schematically illustrates performance of an exemplary soleus contraction from a starting ankle angle to an ending ankle angle with a "good" soleus electromyography signal.

FIGS. 4A, 4B, and 4C schematically illustrate performance of SPUs with different starting ankle angles 316 and performed with different ranges of motion resulting in different quality of soleus contractions as determined by soleus electromyography (EMG). The top view of each figure shows the start position of a soleus push-up, with heel 312 and forefoot 314 down and in contact with a surface 315. It is desirable for the starting ankle angle 316 to be in the range of about 60 to 80 degrees, depending on the user's flexibility, which facilitates a greater range of motion for each SPU contraction. Ankle angle 316 is the angle between foot 300 and shin 306, for example, an ankle angle of 90 degrees is defined as the tibia and sole of the foot at a right angle. The bottom view in each figure shows the ankle angle at the end of the ankle extension, after heel 312 has been raised relative to forefoot 314. FIGS. 4A and 4C illustrate soleus contractions with a good EMG signal. FIG. 4A illustrates user 302 in the seated position with the foot on floor 315 and pulled back positioning the foot under the user and placing ankle angle at 80 degrees. This position may be difficult to achieve due to the user's flexibility and/or the type of chair, sofa, couch, on which the user is sitting. FIG. 4B illustrates the user with the legs extended out, in a more common seated position, and with the foot flat on the floor placing the ankle angle at 110 degrees. With a starting ankle angle 316 of 110 degrees, the ROM of a plantarflexion is limited, resulting in poor soleus activation. FIG. 4C shows a user using a base station 350 to achieve a beneficial starting ankle angle. Base station 350 can be configured in different forms and arranged so that the user can place foot 300 on base 350 with the foot positioned forward of the user's body to achieve a starting ankle angle 316 of between about 60 to 80 degrees. For example, base 350 has a horizontal, planar, bottom surface 318 for resting on the floor and a placement surface 320 extending upward from the bottom surface and configured for placement of the user's forefoot. In FIG. 4C, the placement surface is illustrated as a planar surface, however, it may be a curved surface, such as a base 350 having a semi-circular shape. The placement surface is configured for placement of the user's forefoot on the placement surface a sufficient distance above the floor 15 so that the user's heel can free float without being obstructed by the floor. In some configurations, base 350 may be planar, or substantially planar, for example with the placement surface generally parallel to the floor. As further described below, base 350 may include one or more mechanisms for conveying performance information to the user.

Figure 5:
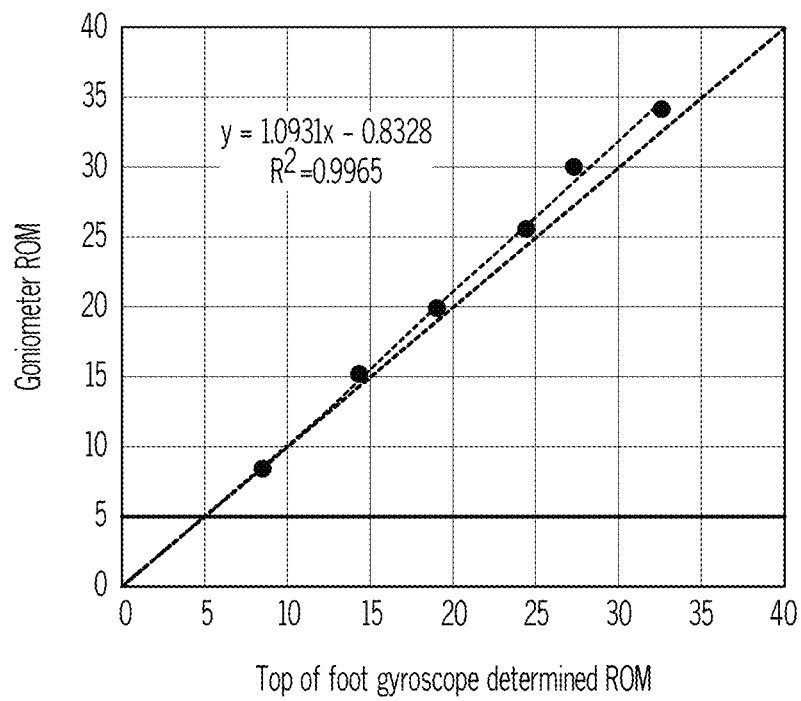
FIG. 5 graphically illustrates goniometer determined range of motion versus a gyroscope determined range of motion for a single gyroscope located on a user's foot.

FIG. 5 graphically illustrates the accuracy of a single gyroscope positioned on a foot in measuring the range of motion of the ankle relative to the range of motion measured with a goniometer. There is high agreement of the goniometer determined ROM and the ROM calculated from a gyroscope of the top of the foot in the tested range of 8 to 33 degrees ROM. The dotted line shows the line of unity which is on the theoretical relationship between perfectly matching measures.

The measurement unit and system can distinguish a SPU contraction motion from other movements. A gyroscope worn on the user's foot, for example as illustrated in FIG. 3, measures rotational movement of the foot about the ankle. FIGS. 6A, 6B, 7A, 7B graphically illustrate rotational movement outputs from a triaxial gyroscope positioned on a user's foot with the X-axis extending laterally, side to side, relative to the foot, the Y-axis extends parallel to the foot, heel to toe, and the Z-axis extends orthogonal to the X-axis and the Y-axis and parallel to gravity. The axes are oriented such that plantarflexions are identified by positive X-axis rotational movements.

Figure 6A:
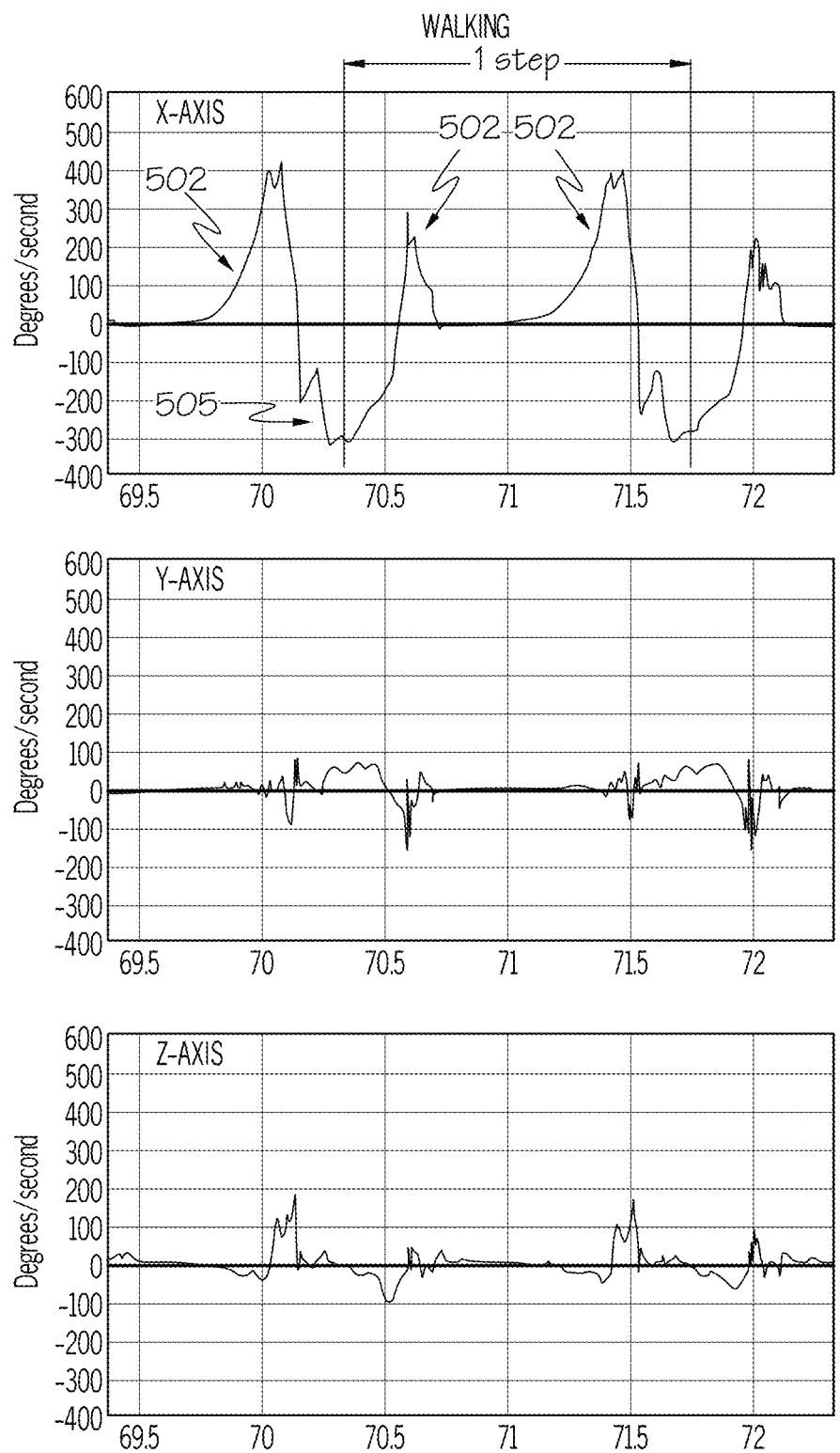
FIG. 6A graphically illustrates exemplary rotational movement of a user's foot, as measured by a triaxial sensor located on the user's foot, when walking.
Figure 6B:
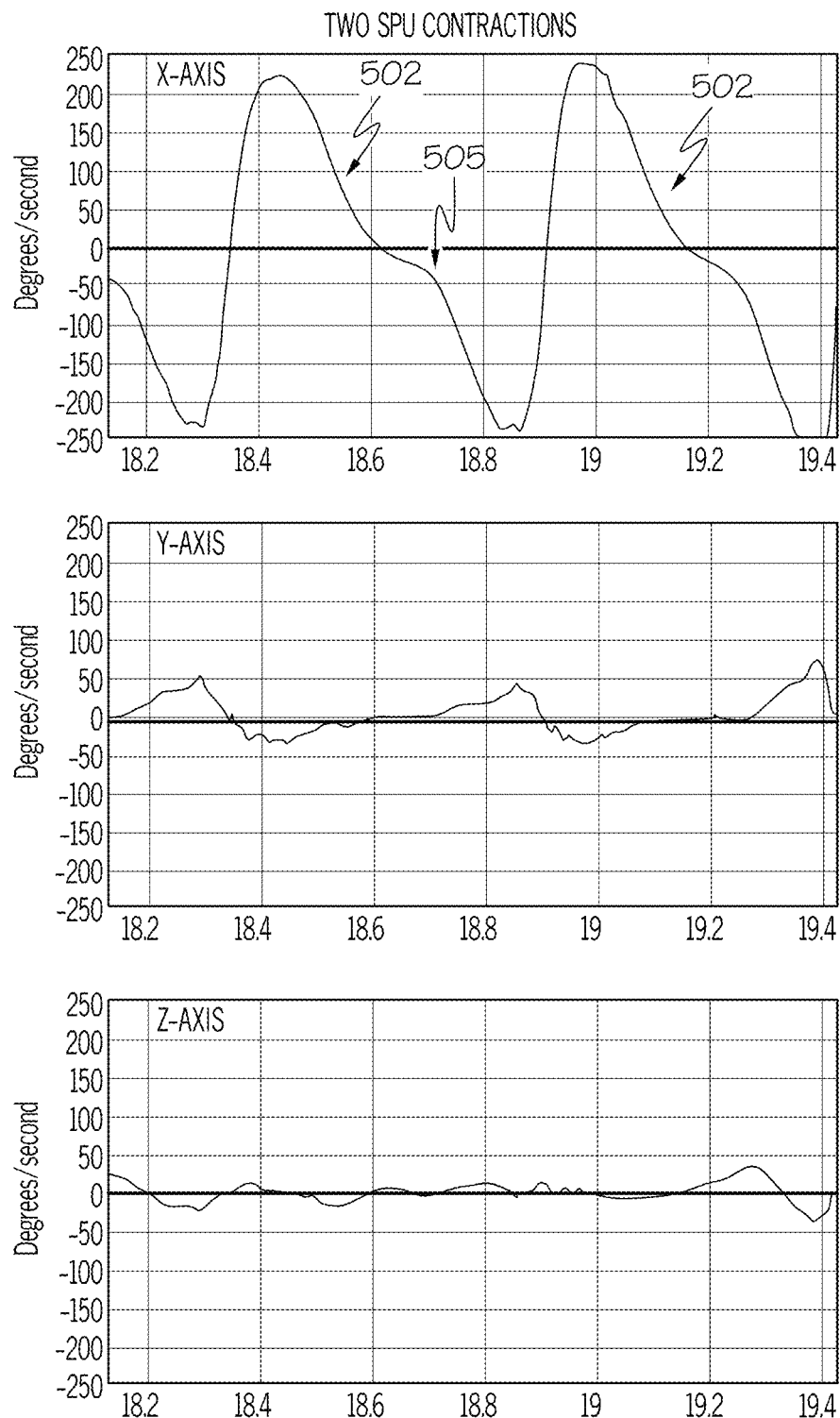
FIG. 6B graphically illustrates exemplary rotational movement of a user's foot, as measured by a triaxial sensor located on the user's foot, when performing ankle extensions deemed soleus contractions.
Figure 7A:
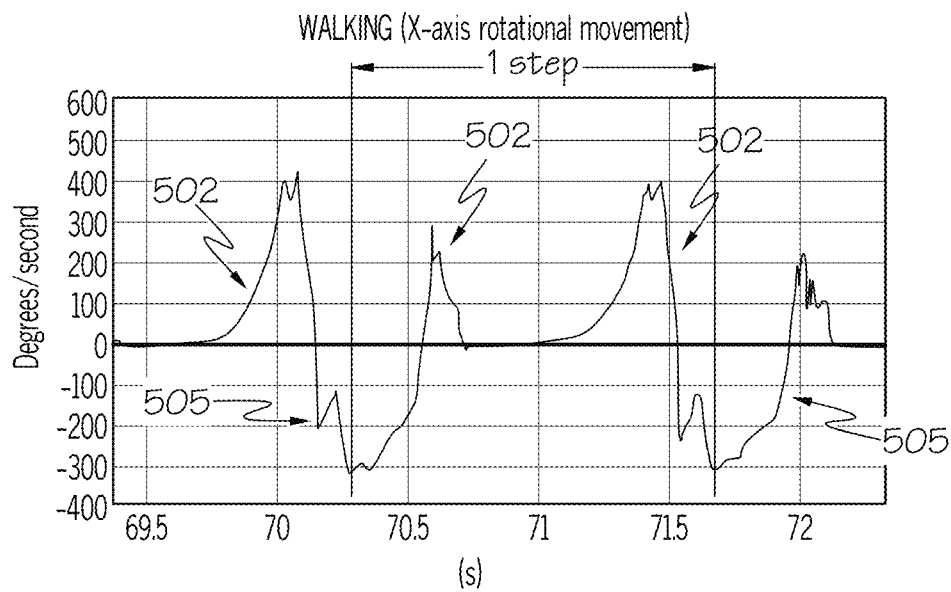
FIG. 7A graphically illustrates exemplary rotational movement about an X-axis extending laterally relative to a user's foot caused by walking.
Figure 7B:
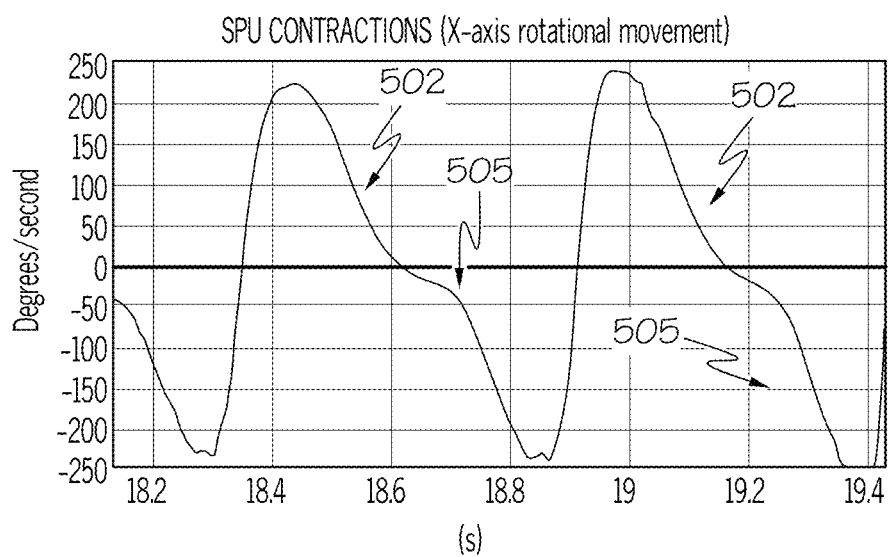
FIG. 7B graphically illustrates exemplary rotational movement about an X-axis extending laterally relative to a user's foot that are deemed soleus contractions.

FIG. 6A graphically illustrates exemplary rotational movement of a user's foot about the X-axis, Y-axis, and Z-axis when walking. FIG. 6B graphically illustrates exemplary rotational movement of a user's foot about the X-axis, Y-axis, and Z-axis when performing ankle extensions that are deemed soleus contractions not produced by walking. FIGS. 7A and 7B are expanded views of the X-axis rotational movement measurements of FIGS. 6A and 6B.

During an SPU contraction, the X-axis rotational movement of the foot is the primary axis of rotation, with relatively less motion about the Y-axis and the Z-axis. As illustrated in FIG. 6B, neither the Y-axis rotational movement nor the Z-axis rotational movement exceed the X-axis rotational movement. For soleus contractions, the Y-axis and the Z-axis rotational movement do not approach the X-axis rotational movement.

The X-axis rotation of the ankle is the movement that causes the leg to rise upward because of ankle extension (plantarflexion) and is indicated by the positive X-axis rotational movement 502. Following this phase of positive, or first direction, rotational movement 502 is a negative rotational movement indicating that the leg is moving in the opposite direction back downward (ankle dorsiflexion). With an SPU contraction, as measured by a gyroscope on the foot, there is a repeating pattern of plantarflexion 502 (positive rotational movement) immediately followed by a period of ankle dorsiflexion 505 (negative rotational movement). A significant contrast with walking (when measured with a gyroscope on the foot) is that in each stride there are two periods of plantarflexion 502 without a negative rotational movement, or without a significant negative rotational movement. Thus, a plantarflexion 502 can be excluded from being deemed a soleus contraction when the plantarflexion is not immediately followed by an ankle dorsiflexion 505 for two consecutive cycles of plantarflexion and dorsiflexion. FIGS. 6A and 7A show an ankle dorsiflexion 505 between adjacent plantarflexions 502, however, there is not an ankle dorsiflexion immediately following each plantarflexion 502 for two consecutive cycles of plantarflexion and dorsiflexion.

FIGS. 7A and 7B show the calculated ROM for plantarflexions 502 and ankle dorsiflexions 505. The range of motion for each plantarflexion 502 peak provides useful information about the rotational movement for defining a soleus contraction. In FIG. 7B, there is a positive X-axis rotational movement equivalent to 33-34 degrees in consecutive plantarflexion 502 peaks and an intervening ankle dorsiflexion 505, 34-degree negative signal. The plantarflexion 502 is immediately followed by an ankle dorsiflexion 505 in two consecutive cycles of plantarflexion and dorsiflexion during the soleus contractions FIG. 7B. The ankle dorsiflexion ROM (34°) is proportional to the adjacent plantarflexion ROM (33° and 34°). In the walking example of FIG. 7A, there is not a negative rotational movement or a minimal negative movement between adjacent plantarflexions 502 in the single step. In some instances, a negative X-axis movement may occur between plantarflexions 502 during walking. An additional step to determine if a rotational movement, is an ankle dorsiflexion for the purposes herein, is to compare the negative rotational movement (velocity or angular displacement) to the adjacent plantarflexions. For example, if the negative rotational movement is not proportional to the adjacent positive rotational movements the negative rotational movement may be discarded as being an ankle dorsiflexion. In an exemplary implementation, when the negative rotational movement is less than about 50 percent of the absolute value of the positive rotational movements of the adjacent plantarflexions the negative rotational movement is discarded as an ankle dorsiflexion.

The disclosed systems can distinguish soleus contractions from other movements with a single sensor 12 worn on the user's foot. Specifically, when a gyroscope is worn on the foot the soleus contraction movement is categorically identified because of a motion that is primarily causing an ankle rotation that is lifting the heel toward the head/upper body while the top of the foot is rotating such that it is starting to point in an anterior direction in front of the body ("X-axis" of rotation is ankle extension/flexion). With each soleus contraction, there is a single ankle extension phase where the X-axis is generating measurable amounts of velocity and ROM. In contrast, during walking each step has two phases of ankle extension in the X-axis rotation, a smaller peak in velocity followed by a larger peak at the end of each stride right before the toe is coming off the floor. Notice in FIG. 6A that the Z-axis is rotating during each step at the end of the stride, unlike what we see after the X-axis ankle extension of an SPU contraction. Although walking and house cleaning or manual labor do frequently involve ankle extension of greater than 3 degrees like a soleus contraction, there is also often substantial rotation of the ankle in the one or both of the other axes (distinguishable from soleus contractions). For example, an ankle rotation may be discarded as a soleus contraction when either the Y-axis rotational movement or the Z-axis rotational movement exceed the X-axis rotational movement. For soleus contractions, the Y-axis and the Z-axis rotational movements do not approach the X-axis rotational movement. For example, during a soleus contraction the Y-axis and Z-axis will be less than about 80 percent of the X-axis rotation. In another example, he Y-axis and Z-axis will be less than about 50 percent of the X-axis rotation. In another example, the Y-axis and Z-axis will be less than about 30 percent of the X-axis rotation.

An ankle rotation may be discarded as a soleus contraction when the medial rotation (Z-axis) and/or lateral rotation (Y-axis) concurrent with the plantarflexion is greater than a limit, e.g., a rotation of 1-degree, 2-degrees, 3-degrees, etc. A lateral or medial rotational limit of about 5-degrees may be used to distinguish clean soleus contractions from other random movements. However, the rotational limit can be increased to provide a greater tolerance to account for anatomical variations from user to user. For example, a lateral or medial angular displacement of about 12 degrees provides a large tolerance for anatomical variations.

There are other distinguishing features measured with the gyroscope that can differentiate soleus contractions that are feasible to include as an extra layer of analytical certainty. In addition to the ROM of the ankle and the angular velocity, the duration of a soleus contraction is often able to discern it from other types of movements. For example, there are some movements like running, brisk walking, and jumping that can have a ROM similar to good quality soleus contraction, but the peak angular velocity is more than in soleus contractions. Rarely has a soleus contraction greater than 300 degrees/sec been measured; yet walking at 3 mph can approach 500 degrees/sec. Testing has shown that car driving is a common behavior with a low ROM of ankle movement caused by vibrations of the road and is also distinguished by rapid series of movements in tandem with a low velocity of each movement.

Examples of common activities that involve movement of the ankle, but in a motion that can be distinguished from soleus contractions with the methods disclosed include: walking, running, and jumping; house cleaning (kitchen work, putting away clothes, sweeping, etc.); manual labor (gardening, painting, construction, etc.); car riding (and other forms of vehicular transport like trains, planes, buses); sitting and fidgeting randomly; and sitting with a commonly performed rapid heel tapping motion that is too rapid.

The ROM of a plantarflexion is physiologically more important that the rate of the performed soleus contractions. However, behaviorally people often tend to think "faster is better," and repetitions are easy to count. People tend to perform plantarflexions faster than they should for the purposes herein. However, a rate is not determinative if quality soleus contractions are achieved.

In an exemplary embodiment, a minimum range of motion for a plantarflexion to be identified as a soleus contraction is about 3 degrees. However, a plantarflexion less than 3 degrees may qualify as a soleus contraction, although a low-quality soleus contraction.

Figure 8:
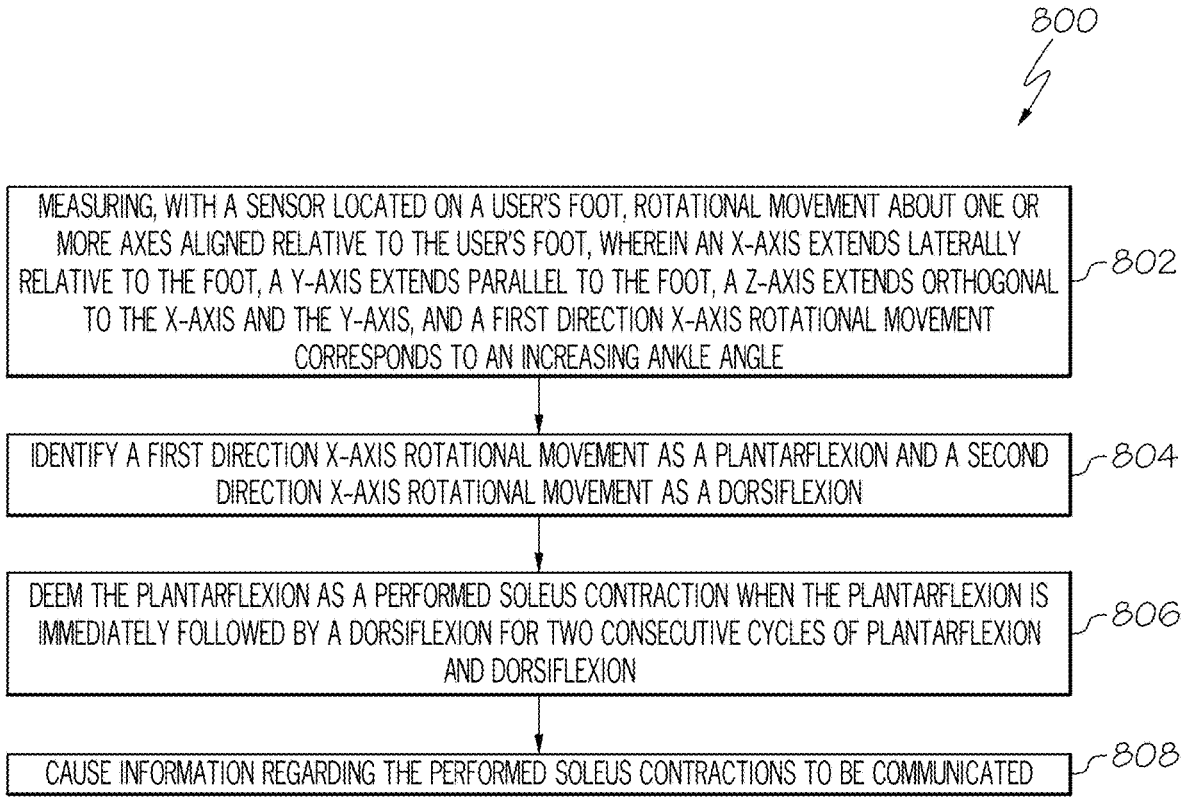
FIG. 8 illustrates an exemplary method, operable by a processor of a measurement unit, for monitoring plantarflexions.

FIG. 8 illustrates an exemplary method 800, operable by a processor of a measurement unit, for monitoring plantarflexions. At block 802, a sensor located on a user's foot measures rotational movement about one or more axes aligned relative to the user's foot, where an X-axis extends laterally relative to the foot, a Y-axis extends parallel to the foot, and a Z-axis extends orthogonal to the X-axis and the Y-axis and where a positive or first direction X-axis rotational movement corresponds to the ankle angle increasing and the second direction X-axis rotational movement corresponding to the ankle angle decreasing. At block 804, a positive X-axis rotational movement is identified as a plantarflexion and a negative X-axis rotational movement is identified as an ankle dorsiflexion. At block 806, the plantarflexion is deemed a performed soleus contraction when the plantarflexion is immediately followed by an ankle dorsiflexion for two consecutive cycles of plantarflexion and ankle dorsiflexion. At block 808, information regarding the performed soleus contractions is communicated.

Figure 9:
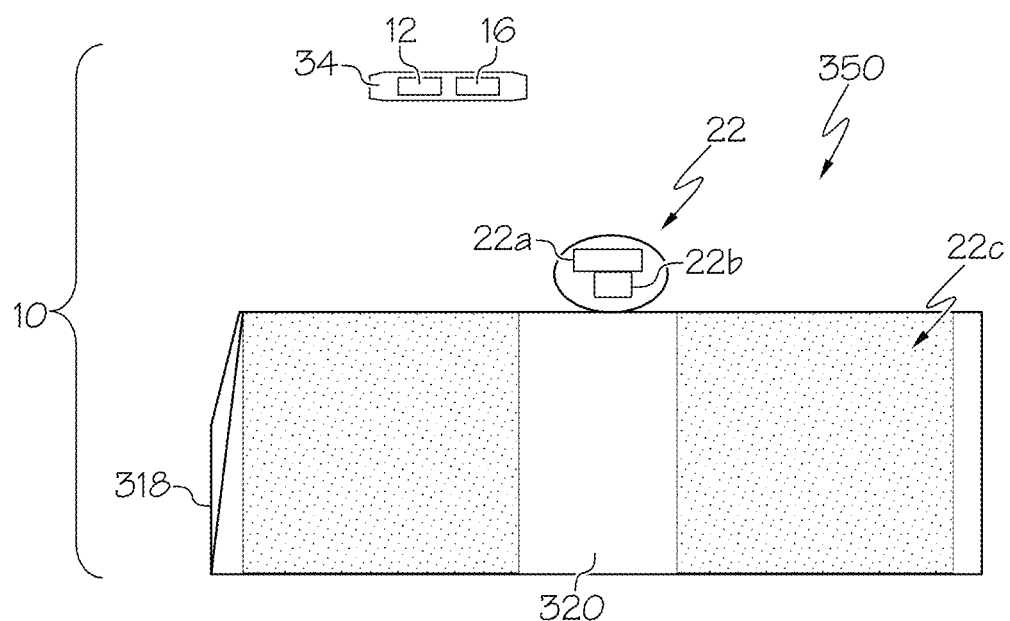
FIG. 9 illustrates an exemplary measurement and tracking system unit incorporating a base foot placement according to one or more aspects of the disclosure.

FIG. 9 is a schematic illustration of an exemplary soleus contraction monitoring unit or system 10. FIG. 9 is described with additional reference in particular to FIGS. 1-3, 4C, and 8. Measurement unit 10 includes a sensor 12 configured to measure rotational movement when positioned on a user's foot with an X-axis oriented laterally across the foot, a Y-axis oriented parallel to the foot, and a Z-axis orthogonal to the X-axis and the Y-axis. The sensor is arranged so that a positive output or first direction X-axis rotation movement corresponds to a plantarflexion where the ankle angle increases. The rotational movement can be measured, for example as angular velocity and/or angular displacement. Measurement system 10 includes a memory 16 (FIG. 1) storing computer-executable instructions 18 (FIG. 1) for controlling a processor 14 to measure an X-axis rotational movement, identify a positive or first direction X-axis rotational movement as a plantarflexion and a negative or second X-axis rotational movement as a dorsiflexion, deem the plantarflexion a performed soleus contraction when the plantarflexion is immediately followed by a dorsiflexion, and cause performance information regarding the performed soleus contractions to be communicated. Utilizing a base 350 whereby the legs extend outward and the user cannot be walking, the soleus contractions can be identified without criteria excluding walking characteristics.

Processor 14 is packaged with sensor 12 in the FIG. 9 embodiment. Sensor 12 is packaged with a fastener 34 to secure the sensor to a user's foot 300 (see, e.g., FIGS. 3 and 4C). Fastener 34 may comprise a loop and hook type feature, strap, sleeve, tie or other mechanism to secure the sensor on the user's foot. The fastener may attach directly to the foot or via a sock or shoe.

A base 350 (e.g., base station) can aid the user in performing the desired soleus contractions and in particular to performing quality soleus contractions. Base 350 includes a bottom surface 318 extending along a horizontal plane and a placement surface 320 extending upward, at an angle greater than zero, from the bottom surface for placement of the user's foot and a communication device 22 configured to communicate the performance information. The placement surface may be parallel to the bottom surface. In the illustrated embodiment, base 350 includes a visual communication device 22a, an audible device 22b, and an active tactile device 22c. The measurement system may include one or more communication devices. The active tactile device 22c may be a pad that communicates selected performance information via physical stimulation, such as vibration, through the user's foot. For example, the active tactile device may communicate that the user is actuating performing the performed soleus contractions.

The base 350 may take various shapes. The illustrated examples are triangular; however, the base is not limited to a triangular arrangement. The placement surface 320 extends upward from the bottom surface so that a user can place the forefoot on the placement surface with the heel able to move free of obstruction from the floor. The placement surface may be angled upward to facilitate placement of the user with the ankle angle within a desired range and the user's legs extended outward.

Examples of performance information that may be communicated include the rate of the performed soleus contractions, an average angular displacement of the performed soleus contractions over a time period, and a time duration the performed soleus contraction have been substantially continuously performed. Substantially continuously performed can include intermittent breaks in the continuous performance, such as breaks that would account for interruptions in measurement data, time periods for adjustment of the user's feet, or other time periods. For example a substantially continuous performance of the soleus contractions may include a time lapse of 30 seconds, one minute, two minutes, etc.

As used herein, the term "substantially," "about," "generally," and similar terms are used as terms of approximation and not a terms of degrees, and are intended to account for the inherent deviations in measured and calculated values that would be recognized by a person of skill in the art. Furthermore, as used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A soleus contraction system to aide a user to properly perform soleus push-ups, the system comprising:
    a base having a base surface extending along a horizontal plane and a placement surface extending upward from the base surface for positioning a foot of the user on the placement surface with an ankle angle of about 60 to 80 degrees when a heel and a forefoot are on the placement surface and the foot is extended forward of a body of the user;
    a communication device located on the base to visually, tactilely, and/or audibly communicate information to the user;
    a sensor configured to measure an angular velocity of a rotational movement of the foot when positioned on the foot, the sensor comprising a fastener configured to attach the sensor to the foot with an X-axis of the sensor oriented laterally across the foot, a Y-axis oriented parallel to the foot, and a Z-axis orthogonal to the X-axis and the Y-axis;

a processor in communication with the sensor, the processor configured to receive the measurement of the angular velocity of the rotational movement;

and a memory storing computer-executable instructions for controlling the processor to:

determine a duration and range of motion of an X-axis rotational movement;

cause to be visually communicated in real time the duration of the X-axis rotational movement and at least one of the angular velocity or the range of motion of the X-axis rotational movement;

identify a positive X-axis rotational movement as a plantarflexion;

identify a negative X-axis rotational movement that immediately follows the positive X-axis rotational movement as an ankle dorsiflexion if an absolute value of the negative X-axis rotational movement is greater than about 50 percent of the positive X-axis rotational movement;

designate the plantarflexion a soleus push-up when the plantarflexion is immediately followed by the ankle dorsiflexion for two consecutive cycles of plantarflexion and ankle dorsiflexion and a duration of the plantarflexion is greater than about 80 msec;

and cause performance information regarding substantially continuous performance of a plurality of the soleus push-ups to be communicated by the communication device during the substantially continuous performance wherein the communication device comprises a vibrating pad on the placement surface, the vibrating pad configured to communicate the performance information via physical stimulation to the foot.

2. The system of claim 1, wherein the communication device comprises a visual display.

3. The system of claim 1, wherein the memory further stores computer-executable instructions for controlling the processor to:

determine a rate of plantarflexions performed per minute;

and exclude plantarflexions from being designated the plurality of the soleus push-ups when the rate is greater than a rate limit, wherein the rate limit is one of:

about 200 per minute;

about 250 per minute;

and about 300 per minute.

4. The system of claim 1, wherein the memory stores computer-executable instructions for controlling the processor to exclude the plantarflexion from being designated the soleus push-up when either a Y-axis rotational movement or a Z-axis rotational movement of the plantarflexion is greater than the positive X-axis rotational movement of the plantarflexion.

5. The system of claim 1, wherein the memory stores computer-executable instructions for controlling the processor to exclude the plantarflexion from being designated the soleus push-up when the angular velocity is greater than about 300 degrees/sec.

* * * * *